United States Patent
Ollivier et al.

(10) Patent No.: US 7,620,457 B2
(45) Date of Patent: Nov. 17, 2009

(54) KIT FOR PENETRATING THE CARDIAC SEPTUM AND FOR THE PLACEMENT OF A TRANS-SEPTAL DEVICE, IN PARTICULAR A STIMULATION PROBE, IN A LEFT CARDIAC CAVITY

(75) Inventors: Jean-Francois Ollivier, Villers LeBacle (FR); Philippe D'Hiver, Chatillon (FR)

(73) Assignee: ELA Medical S.A.S., Montrouge (FR)

( * ) Notice: Subject to any disclaimer, the term of this patent is extended or adjusted under 35 U.S.C. 154(b) by 601 days.

(21) Appl. No.: 10/947,649

(22) Filed: Sep. 22, 2004

(65) Prior Publication Data

US 2005/0085883 A1  Apr. 21, 2005

(30) Foreign Application Priority Data

Sep. 22, 2003  (FR) .................................. 03 11065

(51) Int. Cl.
*A61N 1/00* (2006.01)
(52) U.S. Cl. ...................................................... 607/119
(58) Field of Classification Search ................. 607/119, 607/122, 126–127, 22; 600/375; 606/129
See application file for complete search history.

(56) References Cited

U.S. PATENT DOCUMENTS

| 5,190,528 | A |   | 3/1993  | Fonger et al. ............... 604/171 |
| 5,312,341 | A |   | 5/1994  | Turi ............................. 604/96 |
| 5,687,723 | A | * | 11/1997 | Avitall ......................... 600/374 |
| 5,833,715 | A | * | 11/1998 | Vachon et al. ............... 607/120 |
| 5,873,864 | A | * | 2/1999  | Luther et al. ................. 604/523 |
| 6,547,787 | B1 |  | 4/2003  | Altman et al. ................ 606/41 |
| 6,931,286 | B2 | * | 8/2005 | Sigg et al. .................... 607/120 |
| 6,970,748 | B2 | * | 11/2005 | Haldeman et al. ........... 607/122 |

FOREIGN PATENT DOCUMENTS

FR  2 365 351  9/1976

* cited by examiner

*Primary Examiner*—George R Evanisko
*Assistant Examiner*—Amanda Patton
(74) *Attorney, Agent, or Firm*—Orrick Herrington & Sutcliffe, LLP

(57) ABSTRACT

A kit for penetrating the cardiac septum and for the placement of a trans-septal device, in particular of a stimulation probe, in a left heart cavity. This kit includes a penetration guide (16), a handling stylet, a piercing stylet (38) and a guiding stylet (46). The penetration guide (16) comprises a probe body with a flexible hollow sheath (22) successively receiving these stylets, and a probe-head (18, 24) having an extendable helicoid screw (20) for anchoring to the wall of the septum (10). The piercing stylet (38) presents a sharp distal extremity (44) emerging from the frontal face, through the anchor (20), over a distance at least equal to the local thickness of the septum (10), so as to traverse through the septum. A guiding stylet will be then introduced into the sheath to form, after withdrawal of the penetration guide (16), an axial guide traversing the septum, for the introduction therethrough of a trans-septal device.

14 Claims, 4 Drawing Sheets

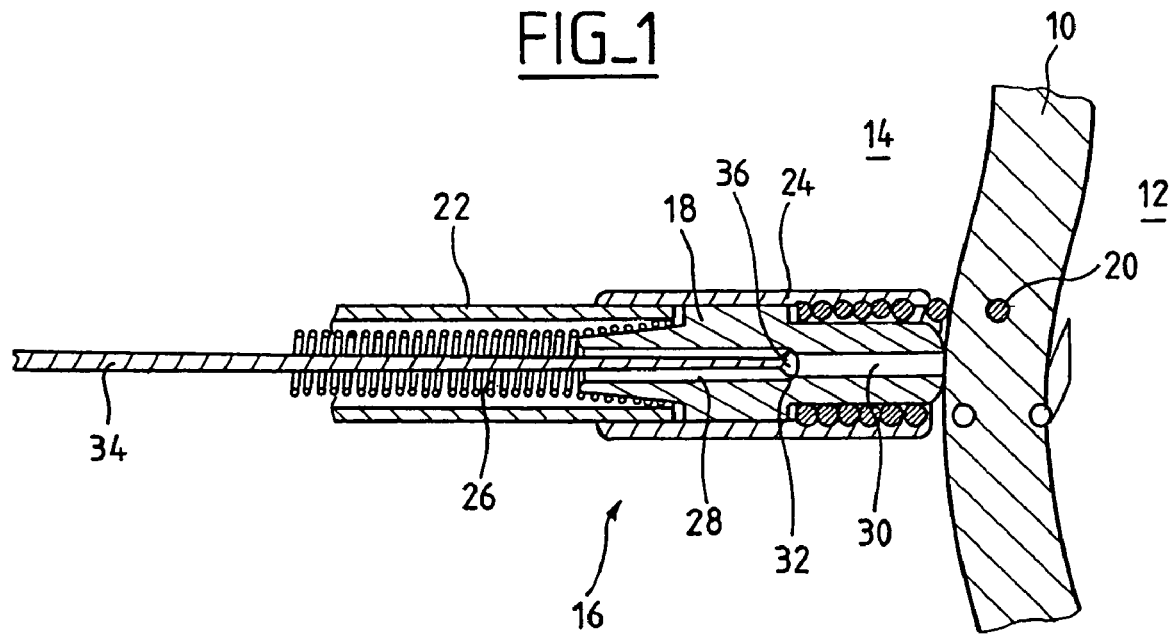
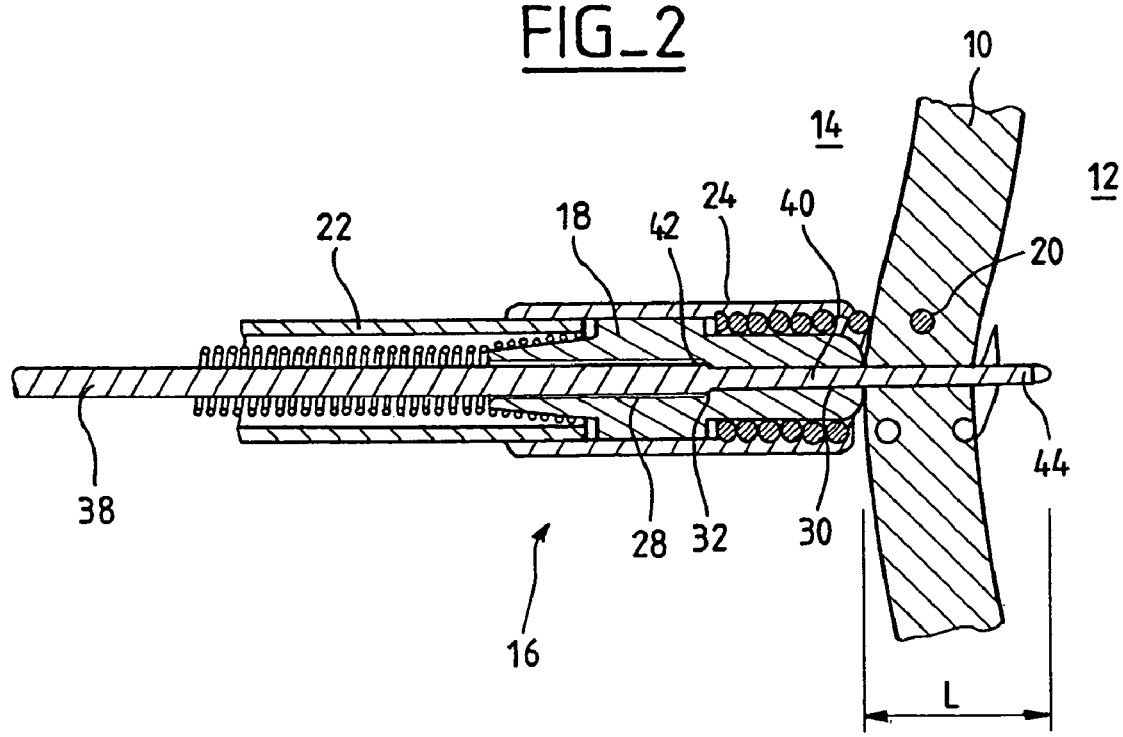

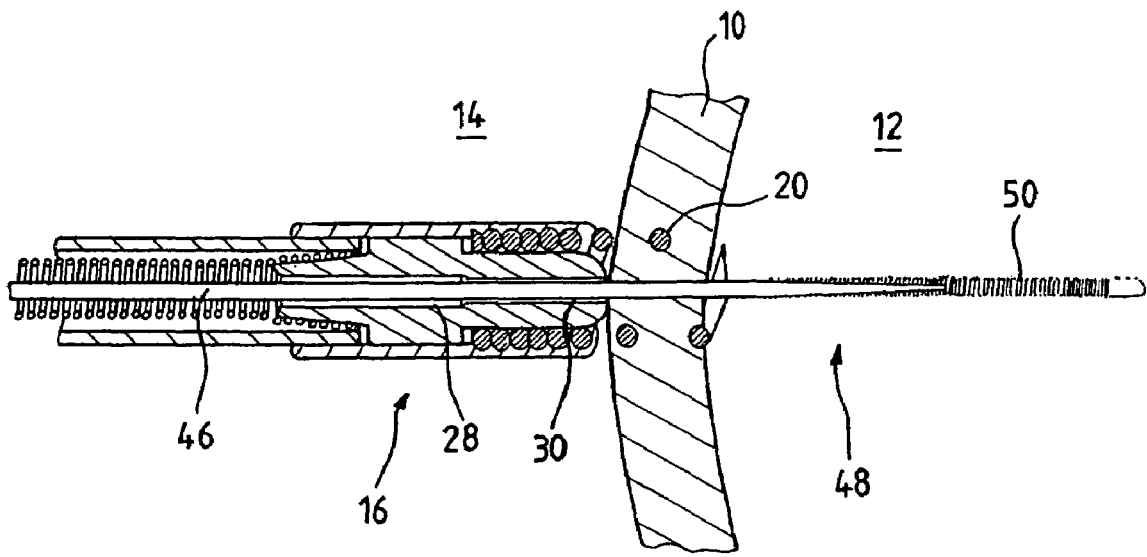
FIG_3
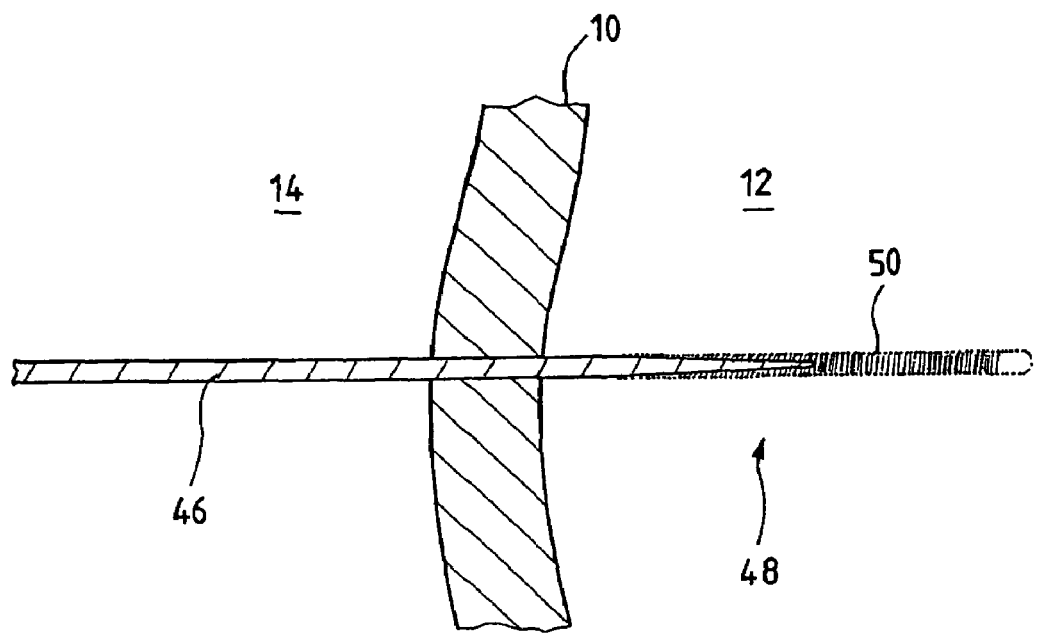
FIG_4

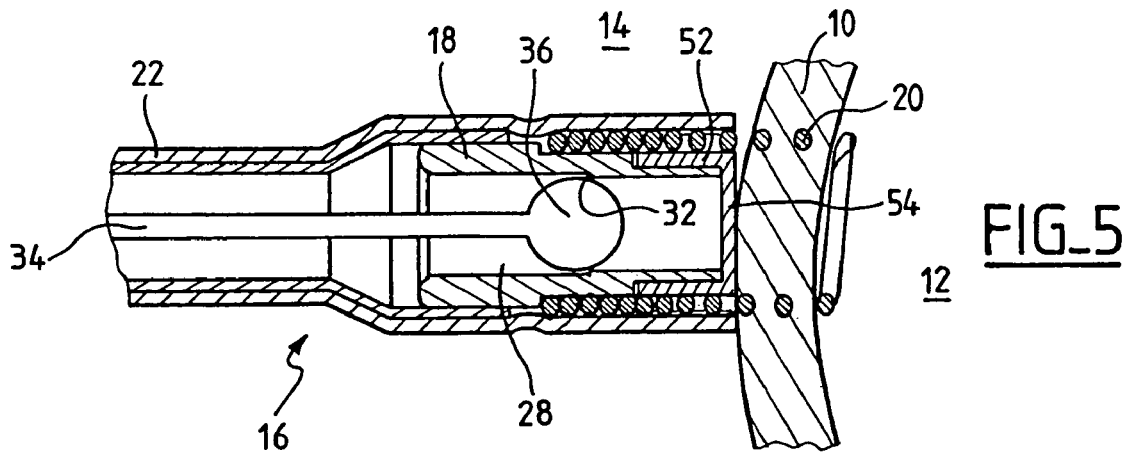
FIG_5
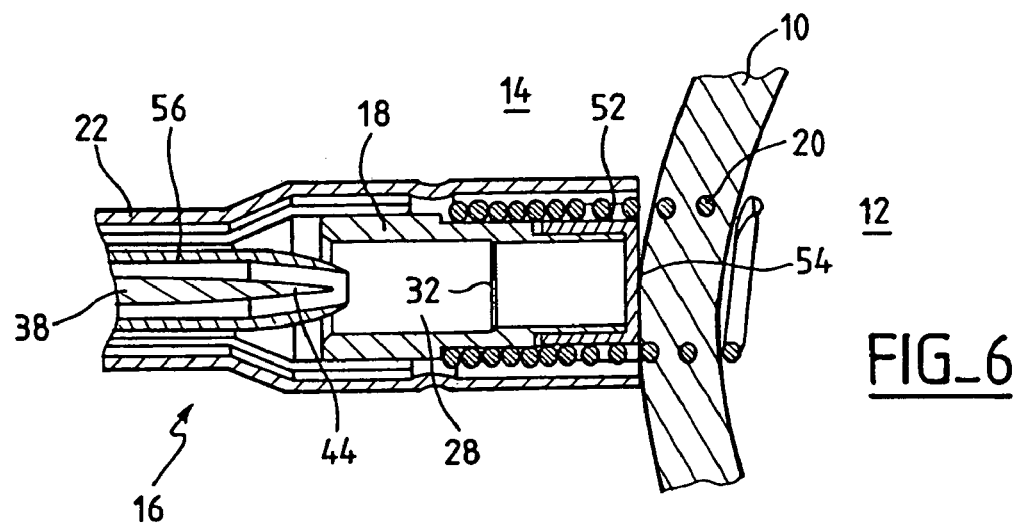
FIG_6
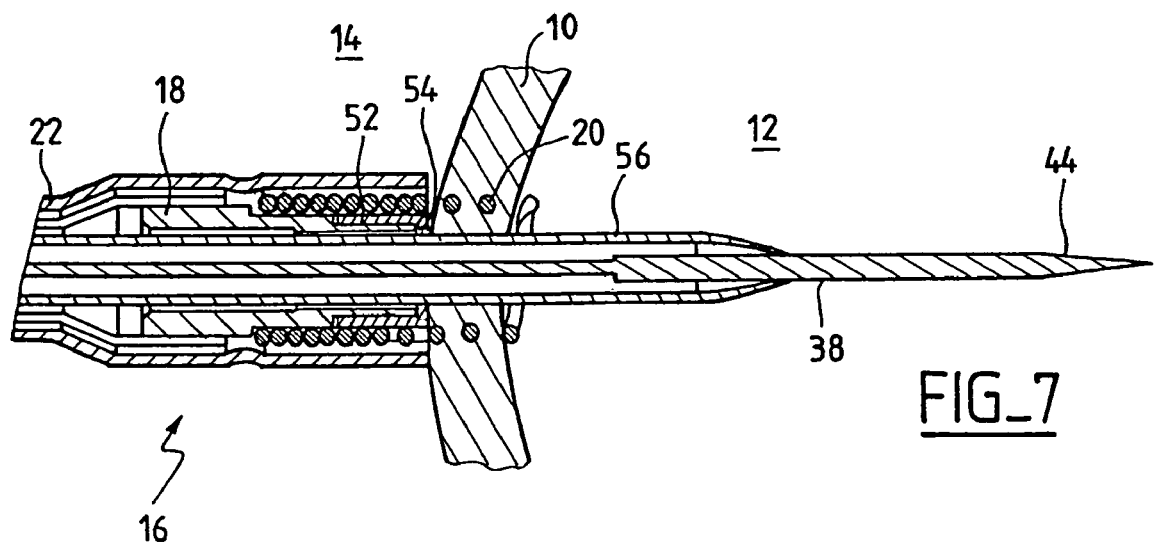
FIG_7

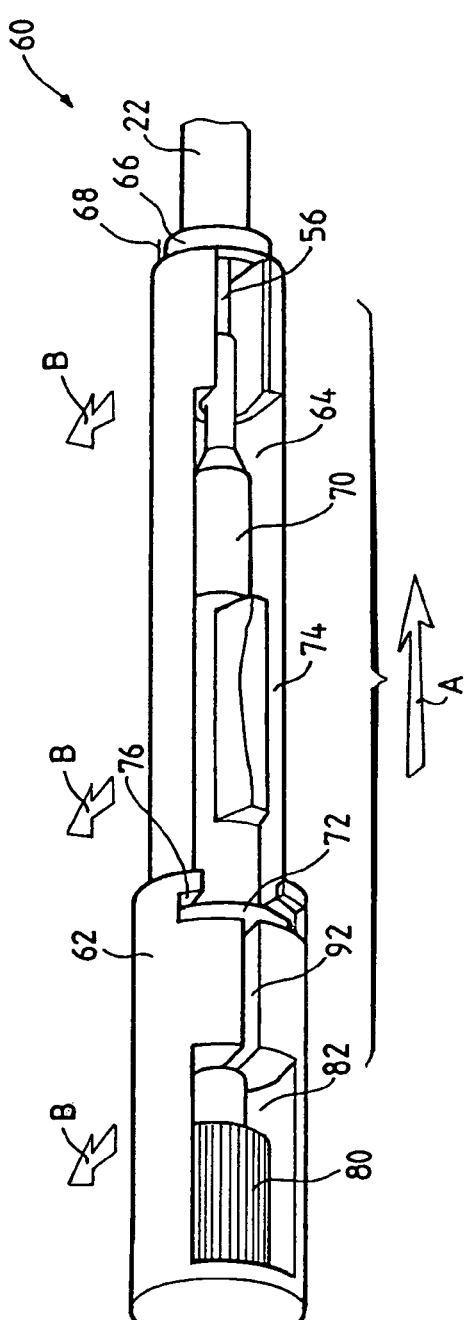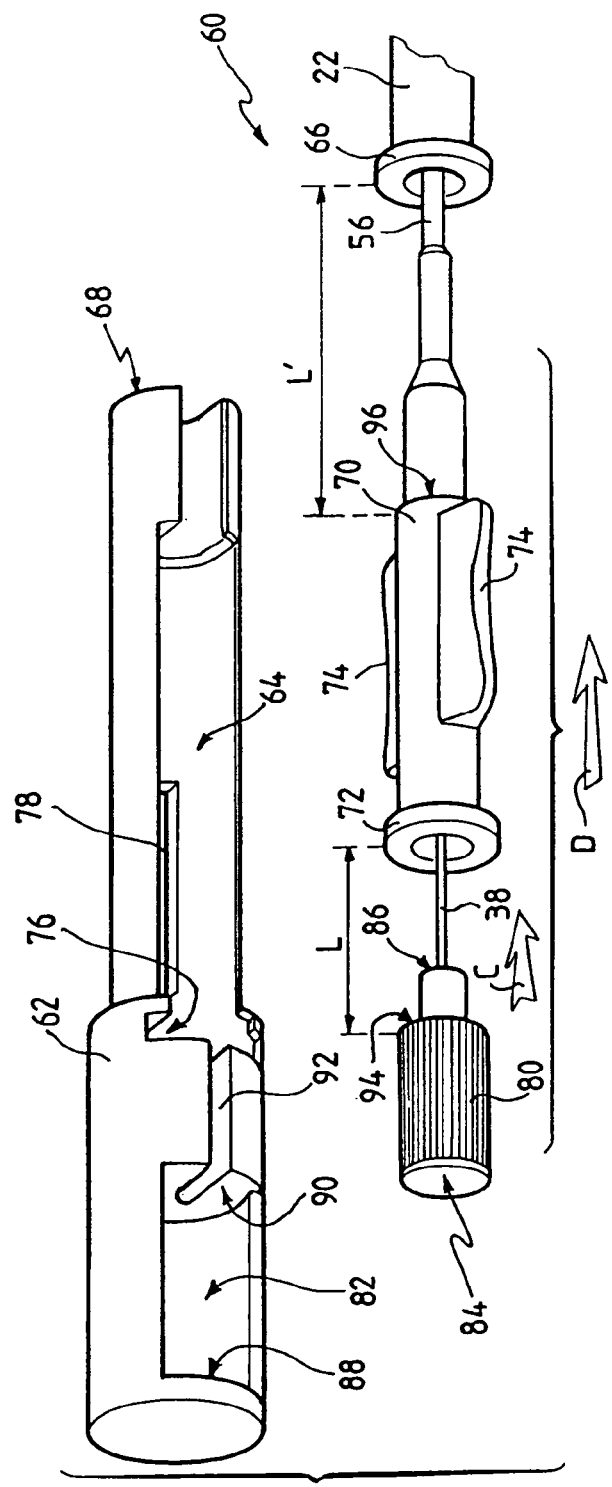

KIT FOR PENETRATING THE CARDIAC SEPTUM AND FOR THE PLACEMENT OF A TRANS-SEPTAL DEVICE, IN PARTICULAR A STIMULATION PROBE, IN A LEFT CARDIAC CAVITY

FIELD OF THE INVENTION

The present invention relates to a kit for penetrating the cardiac septum and for the placement therein of a trans-septal device.

BACKGROUND OF THE INVENTION

For the stimulation of the right cardiac cavities, it typically is sufficient to implant an endocardial probe through the right peripheral venous network. On the other hand, to stimulate the left cardiac cavities, the situation is more complex and the solution most often adopted concerns introducing the stimulation probe through the right atrium and then into the coronary network via the ostium of the coronary sinus. This implant technique is, however, not always realizable, in particular when the configuration of the coronary sinus is too sinuous, or in case of thrombosis (blockage).

Another solution, known as the "trans-septal approach," concerns passing the probe through the interatrial or interventricular wall or "cardiac septum", to stimulate the left cavity (atrium and/or ventricle), according to the configuration and the placement of the probe. This procedure as it is currently employed presents, however, high operational risks, in particular of accidental perforation of the aorta, and/or of dissection of the walls of the right atrium by an unexpected rotatory movement of the septum piercing needle. In any event, this technique is very delicate to implement and requires a great deal of skill from the surgeon who must, to be able to traverse the septum, carry out multiple punctures of the wall, while always making sure of the correct positioning of the probe, with the crossing of the septum to be undertaken only if there remains no doubt about the position or placement of the needle.

U.S. Pat. No. 5,190,528 describes a kit allowing one to introduce trans-septally a catheter in order to access blood in the left atrial cavity, to recycle it towards the arterial circuit via an extracorporal pump. The penetration of the septum is carried out by a needle extending from the extremity of a catheter, which comes to pierce the interatrial septum. A catheter is then advanced over the needle through the septum and then the needle is withdrawn. The handling of such a device is particularly delicate to avoid improper movement, and must be made by an experienced surgeon under fluoroscopic examination in order to determine the position and the distance of the needle relative to the wall to be perforated.

U.S. Pat. No. 5,312,341 describes an improvement in which the trans-septal catheter is equipped with a retention means, for example, in the form of an inflatable collar, to maintain in place the catheter so that its distal extremity remains inside the left atrium. Although this improves safety after the implantation of the catheter, it does not solve the difficulty of the precise penetration of the septum for the placement of the catheter, with the high risks attached to such an intervention.

The present invention is particularly useful for the placement of a probe in a left cardiac cavity, e.g., to stimulate the left cavity using an "active implantable medical device," as such devices are defined by the Jun. 20, 1990 directive 90/385/CEE of the Council of the European Communities, and more particularly a device such as a cardiac pacemaker, a defibrillator and/or a cardiovertor and/or a "multisite" device. But it should be understood that the invention is not limited to the placement of stimulation probes. As it will be understood by a person of ordinary skill in the art, the kit also applies advantageously to any invasive surgical technique that requires traversing the cardiac septum, for example, to carry out clinical investigations in one or the other of the left cardiac cavities. It can also be used in an angioplasty procedure, in particular for operations of mitral valvuloplasty.

OBJECTS AND SUMMARY OF THE INVENTION

It is therefore an object of the present invention is to overcome the difficulties of the known trans-septal techniques, by proposing a kit for penetrating the cardiac septum and allowing for the placement of a trans-septal device that minimizes the invasive character of the intervention.

Advantageously, the present invention avoids the multiple punctures of the wall as known in the prior art and allows a sure penetration once the intervention site on the wall of the septum is defined.

Advantageously also, one will appreciate that kit of the present invention is implemented by techniques that are comparable with techniques already known in the art (in particular, placement of a screw-in stimulation probe by the subclavian approach), in which surgeons are already trained and may be adapted without difficulty for an intervention for penetrating the septum.

To this end, the invention is broadly directed to a kit that includes:

a penetration guide, comprising: a probe-body having a flexible hollow sheath presenting along its length an internal lumen, a proximal extremity able to receive a stylet or a series of stylets successively introduced through the proximal extremity, and a distal extremity; and a probe-head, located at the distal extremity of the flexible sheath and having extending therethrough at an axial bore in communication with the internal lumen of the flexible sheath, the axial bore extending between a proximal end and a distal end, the distal end having a frontal face, the frontal face comprising a means for anchoring the distal end of the penetration guide to the wall of the septum;

a handling stylet, able to be introduced into the lumen of the flexible sheath and the axial bore of the probe-body, said stylet having a distal extremity mobile in translation relative to the penetration guide from the proximal extremity to a first limit position beyond which said handling stylet does not advance, said first limit position being located proximate to the distal end having the frontal face of the probe-body;

a piercing stylet having a sharp distal extremity and able to be introduced into the lumen of the flexible sheath and the axial bore of the probe-body, said piercing stylet sharp distal extremity being mobile in translation relative to the penetration guide from the proximal extremity to a first stop position beyond which the piercing stylet does not advance, the first stop position being located proximate to the distal end having the frontal face of the probe-body, and, in response to an applied additional force being movable from said first stop position toward the distal extremity to a second position, whereby at the second stop position the sharp distal extremity emerges from the frontal face over a length at least equal to the local thickness of the septum, so as to traverse the septum; and a guiding stylet, able to be introduced into the lumen of the flexible sheath and the axial bore of the probe-body, said guiding stylet having a distal extremity that is mobile in translation relative to the penetration guide from the proximal extremity to the distal extremity of the penetration guide until an axial position where the guiding stylet distal extremity emerges from the frontal face over a length at least equal to the local thickness of the septum, so as to form, after withdrawal of the penetration guide, an axial pathway guide from one heart cavity to the other through the septum, for the introduction of the aforesaid trans-septal device.

Preferably, the sharp distal extremity of the piercing stylet passes through the anchoring means in application. This provides accurate placement of the sharp extremity relative to the location where the penetration guide is secured to the septum. In the alternative, other configurations that provide a precise placement of the piercing stylet distal extremity relative to the place where the penetration guide is anchored to the septum may be used. For example, where the anchoring means is secured to the distal end of the probe-head, the probe-head axial bore may be positioned laterally offset from the anchoring means, such that the distal opening of the axial bore opens in the frontal face to be adjacent the septum but the piercing stylet distal extremity does not pass through the anchoring means.

The means for anchoring can in particular include a helicoid (helical) screw interdependent of the probe-head, the screw being mounted in the distal end of the probe head and able to be rotated by an action at the sheath proximal extremity to allow the anchoring of the helicoid screw by screwing in the septal tissue.

The penetration guide preferably includes first means of abutment, to limit the axial movement of the handling stylet beyond the predetermined limit position, and/or a second means of abutment, to limit the axial movement of the piercing stylet to the first stop position and, with the aforementioned applied additional force undergo axial travel to the second stop position. These means of abutment can in particular made by a shrinkage or reduction of the diameter of the axial bore of the probe-head, cooperating with a bulge at the distal extremity of the handling stylet and/or with a shoulder (i.e., a change in cross section dimension) of the piercing stylet. Preferably, the shoulder is proximal to the sharp distal extremity of the piercing stylet.

In an alternative embodiment, the means of abutment can be formed by a thread along a length of the axial bore of the probe-head cooperating with a homologous thread along the handling stylet and/or the piercing stylet. This structure makes it possible to more finely control the applied additional force, in this embodiment a rotational force with the relative movement of the cooperating threads, and the corresponding axial advance of the piercing stylet between the first stop position and the second stop position.

In one particular embodiment, the penetration guide also includes a seal in the axial bore of the probe body at its distal extremity, preferably in the frontal face. The seal is a body that may be penetrated or pierced, yet will continue to act as a plug and prevent body fluids from passing through the interior lumen of the sheath.

In one alternative embodiment, the kit also can include a catheter guide, able to be introduced into the flexible hollow sheath of the penetration guide, and comprising an internal lumen open at its proximal and distal extremities, to receive successively the piercing stylet and the guiding stylet over the entire length of the catheter guide and beyond the distal opening of the catheter guide until in the cardiac cavity.

The kit also can advantageously include a removable handling tool, comprising a internal housing that is laterally open so as to receive simultaneously the proximal extremities of the flexible sheath of the penetration guide, the catheter guide, and the piercing stylet, this internal housing being formed and dimensioned so as to fix these proximal extremities in predetermined relative positions. Such an assembly forms a boring template preventing any excessive penetration of the piercing stylet and/or the catheter guide beyond the wall of the septum after withdrawal of the removable tool and the axial penetration of the piercing stylet and the catheter guide.

BRIEF DESCRIPTION OF THE DRAWINGS

Further benefits, features and characteristics of the present invention will become apparent to a person of ordinary skill in the art in view of the following detailed description of a preferred embodiment of the invention, made with reference to the annexed drawings, in which like reference characters refer to like elements, and in which:

FIG. 1 is a cross-sectional view of a penetration guide in accordance with the invention, equipped with a handling stylet in a configuration corresponding to a first phase of an operation for penetrating the septum;

FIG. 2 is homologous with FIG. 1, showing the penetration guide equipped with a piercing stylet for a second phase of the penetration operation;

FIG. 3 is homologous with FIG. 1, showing the penetration guide equipped with a guiding stylet for a third phase of the penetration operation;

FIG. 4 shows the guiding stylet of FIG. 3 implanted through the wall of the septum, after withdrawing the penetration guide, for a fourth stage of the penetration operation;

FIGS. 5 to 7 are cross-sectional views of a penetration guide according to alternative embodiments of the invention, respectively illustrating a configuration of anchoring the guide, the piercing stylet approaching, and traversing, the septum wall; and FIGS. 8 and 9 illustrate a handling tool useful for the execution of the various stages of penetration, respectively in an initial configuration and a subsequent configuration, once the penetration guide is anchored in the wall of the septum (FIG. 9 also showing in an exploded perspective view various parts of FIG. 8).

DETAILED DESCRIPTION OF THE INVENTION

With reference to FIG. 1, reference 10 indicates the wall of the cardiac septum, for example, in the example described below, the wall separating cavity 12 of the left atrium to cavity 14 of the right atrium. It will be understood, however, that this description can be transposed in a similar way to the penetration of the cardiac septum separating the left ventricle from the right ventricle. Furhter, the description which follows discusses the invention in the context of an intervention concerning passing a stimulation probe through the interatrial wall so as to stimulate a left cavity (ventricle or atrium) by means of the probe. As explained above, this type of intervention is, however, not restrictive, and the kit of the invention also can be used for other types of interventions requiring the penetration of the cardiac septum, for example, the passage of a probe for the measurement of various physiological parameters from the interior of a left cavity, the introduction of a trans-septal catheter to carry out an access to a left cavity, etc.

The kit for penetration of the invention implements a penetration guide 16 having a structure that is comparable in many respects with that of a known stimulation probe known as "screw-in lead", i.e., a probe that is provided at its distal extremity with a helicoid screw presenting a sharpened extremity. The screw allows anchoring the distal extremity in cardiac tissue at the point of contact by a rotational movement imparted by the physician at the proximal extremity and transmitted to probe-head 18, and thus to the anchoring screw, through the sheath connecting the probe-head to the proximal extremity. The method of introducing and fixing such a probe is similar to that of the traditional probes provided with an anchoring screw, and thus are well known in the art.

More particularly, probe-head 18 has a generally cylindrical form, and it is provided at its distal end with a frontal face extremity and with an anchoring screw 20 extending therefrom. At the proximal extremity, probe-head 18 is connected to a flexible hollow sheath 22 (of which only a part is illustrated on the figures) presenting along its length an internal lumen. The external surface 24 of probe-head 18 is a conventional medical grade silicone surface. Anchoring screw 20 is preferably connected to an internal conductor 26 placed in the lumen of sheath 22 and passing through probe-head 18, thus making it possible to collect (detect) an electric signal at the level of the wall of the septum.

Probe-head 18 presents an internal axial bore 28 extending to the frontal face from the body of probe-head 18 and emerging in the center of the bore on the axis of the helicoid anchoring screw 20. Bore 28 is preferably circular in cross section, and generally cylindrical along its axis. The distal portion of bore 28 has an extremity 30 having a smaller diameter so as to form a shrinkage 32, (e.g., in the form of a step transition or other reduction in diameter moving from the proximal portion to the distal portion, as will be discussed below).

According to a first phase of the intervention, a handling stylet 34 is introduced into the lumen of sheath 22. Handling stylet 34 is preferably of the "profiled stylet with ball" type, which is in itself known, i.e., its distal portion is progressively tapered to the extremity which terminates in a bulge 36 or similar blunt structure such as a spherial shape avoiding any risk of piercing or damage of tissue by this extremity. The first phase of the intervention thus concerns placing handling stylet 34 in the lumen of the hollow sheath 22, so as to rigidify the penetration guide. The diameter of bulge 36 is greater than that of the reduced diameter of axial boring 30, such that bulge 36 comes to butt against shrinkage 32 at a first limit position, preventing the handling stylet 34 distal extremity from passing through and extending out of the probe-head distal extremity.

By handling manipulations that are already known, the physician then introduces the probe-head 18 (with handling stylet 34 inserted) into cavity 14 of the right atrium until it abuts against wall 10 of the septum. He then screws the penetration guide 16 on this wall 10 by imparting a rotation to the probe-head 18 that rotates anchoring screw 20, via the sheath 22 from the proximal extremity of the sheath (described below further, with particular reference to FIG. 6, a tool allowing one to carry out this operation). The end of the screwing operation is detected tactilely by the physician in a conventional manner, based on the increased degree of resistance opposing rotation. It is also possible to collect a characteristic electric signal via screw 20 in order to ensure the proper positioning of the probe. This verification being carried out, the handling stylet 34 is then withdrawn and replaced by a piercing stylet 38 for the next phase.

FIG. 2 illustrates piercing stylet 38 introduced into penetration guide 16. Piercing stylet 38 presents a distal portion 40 having a reduced diameter, by a diameter that is smaller than that of the portions 28 and 30 of probe-head 18. A shoulder 42 of the piercing stylet comes into abutment against the interior shrinkage 32 at the junction of the different dimensions of bore portions 28 and 30, so as to limit the length L that the sharp distal extremity 44 of the piercing stylet 38 emerges beyond the frontal face of probe-head 18. When introducing piercing stylet 38, the physician exerts, at the proximal end, repeated pushes on the handle of the stylet. This application of an applied additional force in the axial direction causes, at the distal extremity, a controlled advance of the sharp extremity 44 and a local perforation of the septum (described below, with reference in particular to FIG. 9, a tool allowing to carry out this operation).

Because the precise positioning of piercing stylet 38 by penetration guide 16 is maintained in place by anchoring screw 20, the sharp extremity 44 remains positioned precisely in the axis of anchoring screw 20, which makes it possible to perforate locally and very precisely the septum, without risk of multiple punctures, and without risk of dissection of the wall by an unexpected rotatory movement of the sharp extremity, as could be the case with the prior art procedures implemented until now.

An alternative embodiment (not illustrated) concerns equipping the extremity of the piercing stylet 38 with a male threading, cooperating with a female threading formed in bore 30 that extends to the abutment of shoulder 42. The penetration of the septum is then carried out with a force imparting a relative rotation of the piercing stylet 38 relative to the penetration guide 16, which has the correlative advantage to limit the lengthening of the probe body under the effect of the constraints resulting from the effort for penetrating the septum, as long as the septum is not traversed by the piercing stylet 38.

The traversal of the septum can be controlled under an X-ray monitoring procedure. Once the crossing is carried out (resulting in a configuration corresponding to the illustration of FIG. 2), piercing stylet 38 is then withdrawn and replaced by a guiding stylet 46. It will be noted that any blood flow backward from the left cavity is minimal during this operation, because the hole in the septum is very small.

FIG. 3 illustrates the configuration with guiding stylet 46 introduced into the penetration guide 16 and through septum wall 10. Guiding stylet 46 is, for example, an angioplasty stylet of a traditional type, i.e., a very fine stylet comprising a metal core provided at a distal extremity 48 with a spring 50 having a flexible extremity that avoids any risk of perforation. Guiding stylet 46 is introduced to such a length making it possible to have its distal extremity 48 pass inside the left cavity 12.

The next phase of the intervention concerns, while maintaining in place guiding stylet 46, withdrawing penetration guide 16 by conducting a rotational movement to withdraw anchoring screw 20 from the septum wall 10, and then the withdrawal by a back translation guided along guiding stylet 46. The final configuration thus obtained is that illustrated in FIG. 4, with guiding stylet 46 forming an axial guide from one cavity (right atrium 14) to the other cavity (left atrium 12) through septum wall 10.

Stylet 46 then can be used for an operation that is in itself traditional, in particular, the introduction of a catheter guide (not illustrated) threaded on stylet 46, possibly via dilating, over the entire length of the stylet (a technique known as Over The Wire ("OTW"). Once the catheter guide distal end is extended through the septum to emerge into the left atrium, guiding stylet 46 will be extracted from inside catheter guide, thereby to leave a free pathway through which a probe (or other transeptal device) can be inserted and optionally implanted in the left atrium or the left ventricle.

FIGS. 5 to 7 illustrate an alternative embodiment of a penetration guide 16, where the distal extremity of probe-head 18 is terminated by a body in the shape of a lid or cap having a cylindrical tube 52 and a frontal face 54, the latter comprising a central penetrable area, but which under the initial condition illustrated in FIG. 5, ensures a seal between internal axial bore 28 and 30 of probe-head 18 and the external environment. This seal avoids any blood flow backward towards the interior of the penetration guide during the insertion process.

As it will be understood, the sharp extremity of the piercing stylet, when it is substituted for the handling stylet (illustrated in FIG. 7), will perforate frontal face 54, while remaining at this location, particularly when the piercing stylet itself is withdrawn to insert in its place the guiding stylet.

FIGS. 5 to 7 are cross-sections of an alternative embodiment of the penetration guide according to the invention, respectively illustrating a configuration of (i) anchoring the guide, (ii) advancing the piercing stylet, and (iii) traversing the septum wall by the piercing stylet combined with a catheter guide.

In this embodiment as in the preceding one, the internal axial bore comprises a small shrinkage (or shoulder) 32 (visible in FIGS. 5 and 6) against which the ball or the bulge of extremity 36 of handling stylet 34 is abutted. On the other hand, the lumen of the flexible hollow sheath 22 presents, as well as the internal axial bore portion 28, a diameter that is increased as compared to the preceding embodiment (FIGS. 1-4), so as to allow the introduction not only of the successive stylets (handling stylet, piercing stylet and guiding stylet) but also of a catheter guide 56 (see FIGS. 6 and 7), introduced into the device and through the wall of the septum at the same time as the piercing stylet. More precisely, FIG. 6 illustrates a configuration of the various elements when catheter guide 56 and piercing stylet 38, after being introduced into flexible sheath 22 at its proximal extremity, are in the proximity of internal axial bore 28.

The next stage then concerns, without modifying the position of the catheter guide, to advance the piercing stylet 38 in the distal direction until it comes to perforate, by its sharp extremity 44, the wall 54, with a sealing reinforced at this place by cylindrical tube 52, so as to avoid any blood backward flow in the internal bore 28 of penetration guide 16.

The stage following then concerns advancing simultaneously in the distal direction piercing stylet 38 and catheter guide 56, until the latter traverse through septum wall 10 and emerge inside cavity 12. The configuration of the various elements at the end of this stage is illustrated in FIG. 7.

The next stage (in itself conventional and non illustrated) concerns, while leaving in place catheter guide 56, withdrawing piercing stylet 38, so that after the withdrawal the catheter guide remains, providing a pathway extending between cavity 12 and the outside of the body of the patient. Through this pathway, the surgeon will then be able to introduce the guiding stylet until the latter emerges from the catheter guide in cavity 12. At the end of this operation, the configuration will be similar to that of FIG. 7, but with the guiding stylet (similar to guiding stylet 46 of FIGS. 3 and 4) substituted for the piercing stylet 38.

Then, the physician withdraws the catheter guide. Then he withdraws the penetration guide 16, by rotational movement to unscrew the anchoring screw, followed by a back translation guided along the guiding stylet. The configuration of the various elements during these two last stages will be similar to that as previously discussed with respect to FIGS. 3 and 4.

FIGS. 8 and 9 illustrate a handling tool 60 making it possible to achieve in a precise way the various stages of piercing and the introduction of the catheter guide. FIG. 8 illustrates the set of the various elements in an initial configuration where the handling tool 60 is connected to the penetration guide, and FIG. 9 illustrates a configuration of the subsequent stage, once the penetration guide is anchored in the wall of the septum, showing the various parts of the combination in an exploded view.

Handling tool 60 includes a removable tool 62, combined with the various elements forming the proximal extremities of (1) sheath 22 extending from the penetration guide, (2) catheter guide 56, and (3) piercing stylet 38. More precisely, removable tool 62 comprises an internal housing 64 laterally open so as to receive the various above-mentioned elements with a particular relative axial positioning. FIG. 8 illustrates the removable tool 62 with these various elements placed in the internal housing 64, and FIG. 9 shows these same elements in the relative positions that they occupy just after the withdrawal of the removable handle by being taken away in a radial direction (indicated by arrows B in FIG. 8).

Flexible sheath 22 of the penetration guide 16 terminates at the proximal side in a flange 66 likely to come into abutment against a distal face 68 of removable tool 62. Catheter guide 56 emerges from flexible sheath 22 in the proximal direction, where it is extended by a thickened body 70 terminating at the proximal end by a flange 72. Body 70 is equipped with lateral wings 74 that make it easier for the physician to handle. Flange 72 is placed in a homologous cavity 76 within removable tool 62, and it is envisaged to have in the latter a slot opening 78 for the passage of one of the wings (the other wing being positioned on the side of the lateral opening in the internal housing 64 of the removable handle).

The piercing stylet 38 is terminated at its distal end by an operating handle 80 which can be received in a cavity 82 homologous within removable tool 62. Operating handle 80 has a proximal side 84 and a distal side 86, the extremities of which come to be placed against opposite homologous surfaces 88 and 90, respectively, of cavity 82. A longitudinal slit 92, open laterally in the same way as internal housing 64, connects cavities 82 and 64 by receiving the part of the piercing stylet 38 included between the operating handle 80 and flange 72 of catheter guide 56.

The sequence of the operation is as follows. Initially, the unit is assembled as illustrated in FIG. 8, where the various elements are retained in given relative positions, imposed by the geometry of the cavities of the removable tool 62. The axial position of the piercing stylet 38 and catheter guide 56, between them and compared to the penetration guide 16, corresponds to that illustrated in FIG. 6, i.e., tip 44 of piercing stylet 38 does not emerge from catheter guide 56, and catheter guide 56 is in a withdrawn position compared to the plane of the distal extremity of penetration guide 16. Piercing stylet 38 and catheter guide 56 are fixed in position compared to each other by the removable tool 62. The surgeon can then introduce this unit into flexible sheath 22 until the distal face 68 of tool 62 comes into abutment against flange 66 from the flexible sheath 22 (arrow A of FIG. 8). The various elements are then presented in the form illustrated in FIG. 8.

The next stage concerns withdrawing tool 62, simply by a side displacement (arrows B of FIG. 8). The various elements are presented then in the form illustrated in FIG. 9.

The next stage involves inserting handle 80 of piercing stylet (arrow C of FIG. 9), thus making it possible at the proximal extremity to perforate the septum. This is done without modifying the position of catheter guide 56. The penetration depth of the piercing stylet 38 is precisely defined by the dimension L defined between flange 72 and face 94 of operating handle 80. This dimension L is defined by the geometry of the removable tool 62 when constructed with these two elements.

The stage following thereafter concerns inserting the "piercing stylet-catheter guide" sub-assembly (arrow D of FIG. 9) inside the flexible sheath 22 of the penetration guide, so as to advance simultaneously these two elements until their distal ends both emerge beyond the wall of the septum, into cavity 12 (i.e., in the illustrated position FIG. 7). Here still, the penetration depth is defined by dimension L', between flange 66 of flexible sheath 22 and a face 96 at the proximal end of thickened body 70 of catheter guide 56, this dimension also being defined by the geometry of the internal housing of the removable tool 62.

As one will have included it, the removable tool 62 makes it possible to fix the various elements (flexible sheath 22 interdependent of the penetration guide 16, catheter guide 56 and piercing stylet 38) in predetermined relative positions, thus providing for preventing any excessive penetration of the piercing stylet and/or the catheter guide inside the cavity 12 after withdrawal of the tool and axial translation of the piercing stylet and the catheter guide.

One skilled in the art will appreciate that the present invention can be practiced by other than the described embodiments, which are presented for purposes of illustration and not of limitation.

We claim:

1. A kit for penetrating a cardiac septum and placing a trans-septal device in a left cardiac cavity, comprising:
   a penetration guide having:
      a probe-body including a flexible hollow sheath having an internal lumen, a proximal extremity, and a distal extremity, wherein said proximal extremity is able to receive, separately, a handling stylet, a piercing stylet, and a guiding stylet introduced at said proximal extremity; and
      a probe-head positioned at the distal extremity of the sheath having an axial bore in communication with the internal lumen of the sheath, a distal end including a frontal face, and means for anchoring the probe-head to the septum wall, wherein the axial bore contains a shrinkage;
   a handling stylet having a distal extremity able to be introduced into the lumen of the sheath and the axial bore of the probe-head, and movable in translation relative to the penetration guide from said sheath proximal extremity to the shrinkage, beyond which said handling stylet does not advance;
   a piercing stylet capable of penetrating through the septum wall, comprising a sharp distal extremity, able to be introduced into the lumen of the sheath and the axial bore of the probe-head, and movable in translation relative to the penetration guide from said sheath proximal extremity to a first axial stop position in said probe-head axial bore, beyond which said piercing stylet does not advance without an applied additional force, and a second axial stop position distal to said first axial stop position, in response to said applied additional force, to provide a controlled additional axial translation moving said piercing stylet from said first axial stop position to said second axial stop position to cause the sharp distal extremity to emerge from the frontal face of said probe-head to traverse said septum, wherein said first and second axial stop positions are separated by distance at least equal to the local thickness of the septum; and
   a guiding stylet having a flexible distal extremity able to be introduced into the lumen of the sheath and the axial bore of the probe-body, and movable in translation relative to the penetration guide from the sheath proximal extremity to an axial stop position where said guiding stylet emerges from the frontal face of the probe-head over a length at least equal to the local thickness of the septum, so as to form, after withdrawal of the penetration guide, an axial pathway through said septum, through which a trans-septal device may be guided by the guiding stylet.

2. The kit of claim 1 wherein said probe-head axial bore is positioned relative to said anchoring means to pass said piercing stylet sharp distal extremity through said anchoring means.

3. The kit of claim 1, wherein the anchoring means comprises a helicoid screw extending from the probe-head frontal face, said screw being rotatable by a rotation of the proximal end of said flexible sheath to screw into said septum tissue.

4. The kit of claim 1, wherein the penetration guide further comprises a first means of abutment, cooperating with said handling stylet, to limit the axial movement of the handling stylet beyond said shrinkage.

5. The kit of claim 4, wherein the axial bore further comprises a first section having a first minimum dimension and a second section having a second minimum dimension, wherein the first abutment means further comprises a transition between said first and second minimum dimensions of said axial bore, wherein said handling stylet distal extremity comprises a bulge having a dimension that is less than said first minimum dimension and greater than said second minimum dimension.

6. The kit of claim 4, wherein the first abutment means further comprises a length of female thread disposed in the axial bore of the probe-head and a cooperating male thread homologous on the exterior of the handling stylet.

7. The kit of claim 1, wherein said piercing stylet has a transition in thickness and wherein the penetration guide further comprises a second means of abutment, cooperating with said piercing stylet transition in thickness to limit the additional axial translation of the piercing stylet beyond said second stop position.

8. The kit of claim 7, wherein the axial bore further comprises a first section having a first minimum dimension and a second section having a second minimum dimension, wherein the second abutment means further comprises a transition between said first and second minimum dimensions, wherein said piercing stylet further comprises a transition in thickness defining a dimension that is greater than said second minimum dimension.

9. The kit of claim 7, wherein the second abutment means further comprises a length of female thread disposed in the axial bore of the probe-head and a cooperating male thread homologous on the exterior of the piercing stylet.

10. The kit of claim 9 wherein said female thread has a length corresponding to said distance between said first and second stop positions.

11. The kit of claim 9 wherein said female thread has a terminus as a position corresponding to the second stop position.

12. The kit of claim 1, wherein the penetration guide further comprises a penetrable body able to seal the axial bore of the probe-head, said penetrable body being positioned proximate to the probe head frontal face.

13. The kit of claim 12, further comprising:
   a removable handling tool comprising an internal housing laterally open so as to receive simultaneously at the proximal end of the penetration guide, the proximal extremities of the flexible sheath, the catheter guide, and the piercing stylet, said internal housing being formed and dimensioned so as to fix said proximal extremities in predetermined relative positions, and thus forming a boring template preventing any excessive penetration of the piercing stylet and the catheter guide beyond the wall of the septum after withdrawal of the removable handle and axial translation of the piercing stylet and the catheter guide.

14. The kit of claim 1, further comprising:
a catheter guide, able to be introduced into the flexible hollow sheath of the penetration guide and comprising an internal lumen having a distal opening and a proximal opening able to receive successively the piercing stylet and the guiding stylet for passage through the entire length of the catheter guide and beyond the distal opening in the cardiac cavity.

* * * * *